United States Patent
Simmons

(10) Patent No.: US 11,273,078 B2
(45) Date of Patent: Mar. 15, 2022

(54) REPLACEABLE DRESSING AND METHOD FOR VIEWING A TISSUE SITE

(71) Applicant: KCI Licensing, Inc., San Antonio, TX (US)

(72) Inventor: Tyler H. Simmons, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 524 days.

(21) Appl. No.: 16/302,563

(22) PCT Filed: May 10, 2017

(86) PCT No.: PCT/US2017/031923
§ 371 (c)(1),
(2) Date: Nov. 16, 2018

(87) PCT Pub. No.: WO2017/200814
PCT Pub. Date: Nov. 23, 2017

(65) Prior Publication Data
US 2019/0167483 A1 Jun. 6, 2019

Related U.S. Application Data

(60) Provisional application No. 62/339,246, filed on May 20, 2016.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61F 13/0266* (2013.01); *A61M 1/90* (2021.05)

(58) Field of Classification Search
CPC ............ A61F 13/00068; A61F 13/0216; A61F 2013/0057; A61F 13/0259; A61F 13/0263; A61F 13/0266; A61M 1/0088
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Ariana Zimbouski

(57) ABSTRACT

Provided are systems, dressings, and methods suitable for treating a tissue site, such as an incision or linear wound. The systems, dressings, and methods relate to a dressing assembly that may include a dressing bolster, sealing members that cover the tissue site and contain the dressing bolster, and a dressing attachment device. The dressing assembly also includes a base layer comprising a sealing member and a base attachment device for releasably coupling the base layer to the epidermis, wherein the dressing attachment device that may releasably coupled to the sealing member base layer. The dressing assembly may also include sealing ring that may be adapted to provide a fluid seal around the
(Continued)

tissue site, and to absorb fluids from the tissue site. Other systems, apparatuses, and methods are disclosed.

29 Claims, 5 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,086,763 A * | 2/1992 | Hathman | A61F 13/0246 128/887 |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 7,922,703 B2 * | 4/2011 | Riesinger | A61M 27/00 604/305 |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0216169 A1 * | 8/2009 | Hansen | A61F 13/0213 602/48 |
| 2014/0163491 A1 | 6/2014 | Schuessler et al. | |
| 2014/0358058 A1 * | 12/2014 | Nelson | A61F 13/00068 602/48 |
| 2015/0057624 A1 * | 2/2015 | Simmons | A61F 13/0223 604/319 |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |

(56) References Cited

FOREIGN PATENT DOCUMENTS

| | | |
|---|---|---|
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds" Vestnik Khirurgi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al.; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

REPLACEABLE DRESSING AND METHOD FOR VIEWING A TISSUE SITE

RELATED APPLICATION

This application is a U.S. National Phase Entry of International Patent Application No. PCT/US2017/031923, filed May 10, 2017, which claims the benefit, under 35 U.S.C. § 119(e), of the filing of U.S. Provisional Patent Application Ser. No. 62/339,246, entitled "Replaceable Dressing and Method for Viewing A Tissue Site" filed May 20, 2016, which is incorporated herein by reference for all purposes.

BACKGROUND

This application relates generally to medical treatment systems and, more particularly, but not by way of limitation, to reduced pressure dressings, systems, and methods for treating wounds including linear wounds.

Clinical studies and practice have shown that providing a reduced pressure in proximity to a tissue site may augment and accelerate the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") may provide a number of benefits, which may include faster healing and increased formulation of granulation tissue. Typically, reduced pressure is applied to tissue through a porous pad or other manifold device. The porous pad may distribute reduced pressure to the tissue and channel fluids that are drawn from the tissue.

SUMMARY

According to an illustrative embodiment, provided is a system for treating a tissue site that may include a dressing assembly and a reduced-pressure source. The dressing assembly may include a dressing bolster, a comfort layer, a first sealing member, a second sealing member, and a first attachment device. The dressing bolster may have a first side and a second side. The comfort layer may be coupled to the second side of the dressing bolster. The first sealing member may cover the first side of the dressing bolster. The second sealing member may cover a portion of the second side of the dressing bolster and extend outward from the dressing bolster to form a drape extension. A portion of the first sealing member may be coupled to the second sealing member. The first attachment device may be coupled to the second side of the second sealing member, wherein the first sealing member, the second sealing member, and the sealing ring may be configured to provide a sealed space over the tissue site.

The dressing assembly may further comprise a base layer including a third sealing member having a first side and a second side including a viewing aperture extending through the third sealing member and wherein the first attachment device is adapted to be releasably coupled to the first side of the third sealing member. The base layer may further include a second attachment device coupled to the second side of the third sealing member and adapted to be releasably coupled to the tissue around the tissue site as defined by the viewing aperture. The reduced-pressure source may be configured to be coupled in fluid communication with the sealed space. The second attachment device has a peel strength and the first attachment device has a peel strength, wherein the peel strength of the second attachment device may be greater than the peel strength of the first attachment device. For example, the first attachment device may have a peel strength less than or equal to about 2.0N/25 mm, and the second attachment device may have a peel strength greater than or equal to about 4.0N/25 mm.

According to another illustrative embodiment, provided is a system as described above wherein the dressing assembly may further include a sealing ring disposed adjacent to the second side of the dressing bolster and may be comprised of a hydrocolloid including an absorbent. The first sealing member, the second sealing member, and the sealing ring may be configured to provide a sealed space over the tissue site. The reduced-pressure source may be configured to be coupled in fluid communication with the sealed space.

According to another illustrative embodiment, provided is a system for treating a tissue site that may include a dressing assembly, a sealing member, and a reduced-pressure source. The dressing assembly may include a dressing bolster, a comfort layer, and a sealing ring. The dressing bolster may have a first side and a second side. The comfort layer may have a first side and a second side, and the first side of the comfort layer may be coupled to the second side of the dressing bolster. The sealing ring may be coupled to the second side of the comfort layer, and the sealing ring may include an absorbent. The sealing member may be configured to cover the dressing assembly and to create a sealed space between the dressing assembly and the tissue site. The reduced-pressure source may be configured to be coupled in fluid communication with the sealed space.

According to another illustrative embodiment, provided is a dressing assembly for applying to a tissue site that may comprise a dressing bolster having a first side and the second side, and a sealing member having a first side and a second side configured to cover the dressing bolster and to create a sealed space over the tissue site. The dressing assembly may further comprise a dressing attachment device coupled to the second side of the sealing member. The dressing assembly may further comprise a base member having a first side and a second side, the first side adapted to be releasably coupled to the sealing member by the dressing attachment device, and a base attachment device coupled to the second side of the base member and adapted to be releasably coupled to tissue surrounding the tissue site. The base attachment device has a peel strength and the dressing attachment device has a peel strength, wherein the peel strength of the base attachment device may be greater than the peel strength of the dressing attachment device. For example, the dressing attachment device may have a peel strength less than or equal to about 2.0N/25 mm, and the base attachment device may have a peel strength greater than or equal to about 4.0N/25 mm. In another example embodiment, the base attachment device and the dressing attachment device each has a peel strength wherein a ratio of peel strength base attachment device to the peel strength of the dressing attachment device is greater than about 2.0.

According to another illustrative embodiment, provided is a method for treating a tissue site that may include disposing a dressing assembly proximate to the tissue site. The dressing assembly may include a dressing bolster, a sealing member including a dressing attachment device, a base member including a base attachment device, and a sealing ring. The method may further comprise positioning the base attachment device on tissue surrounding the tissue site to releasably couple the base member to the tissue surrounding the tissue site. The method may further comprise covering the dressing bolster and the tissue site with the sealing member to releasably couple the dressing attachment device to the base member to form a sealed space between the sealing member and the tissue site. The method may further comprise extracting fluid from the tissue site into the dressing assembly. The method may further comprise removing the sealing member from the base member without removing the base member from the tissue surrounding the tissue site. The method may further comprise replacing the sealing member on the base member after inspecting the tissue site through a viewing aperture.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the subject matter of this disclosure. Other embodiments may be utilized, and logical, structural, mechanical, electrical, and chemical changes may be made without departing from the scope of this disclosure. To avoid detail not necessary to enable those skilled in the art to practice the embodiments described herein, the description may omit certain information known to those skilled in the art. Therefore, the following detailed description is non-limiting, with the scope of the illustrative embodiments being defined by the appended claims.

Figure 1:
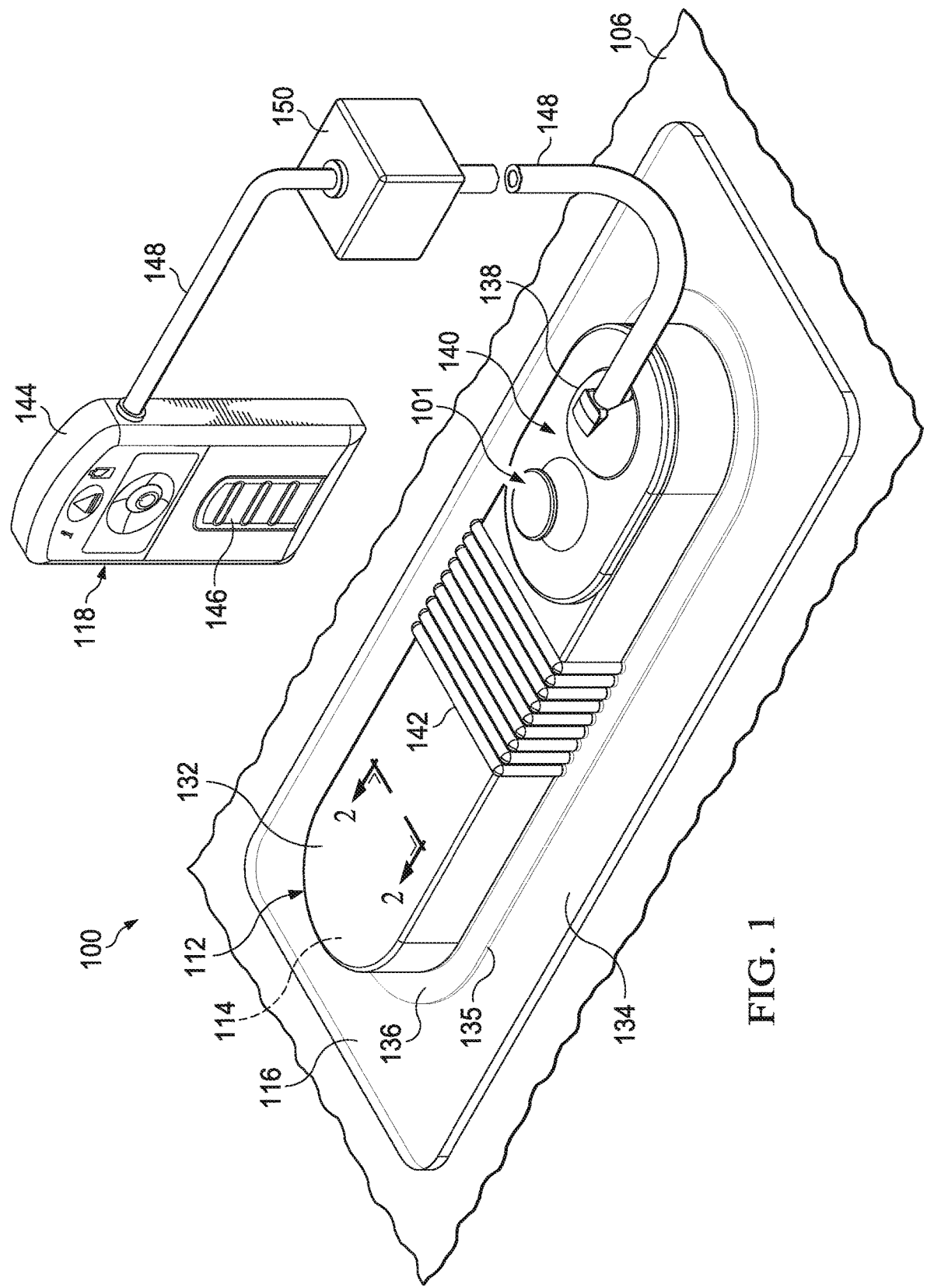
FIG. 1 is a perspective view of an illustrative embodiment of a system for treating a tissue site.
Figure 2:
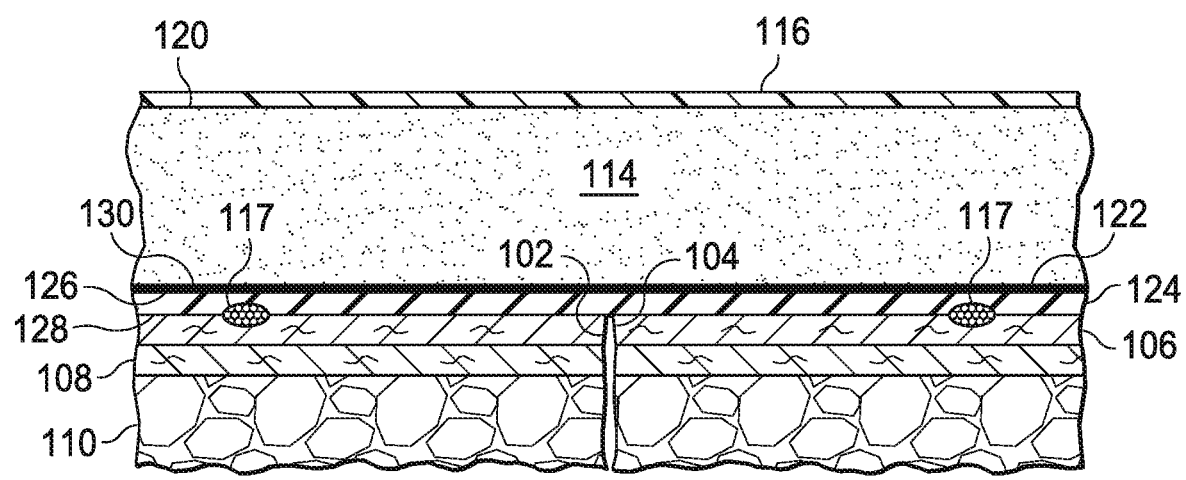
FIG. 2 is a cross-section of a portion of an illustrative embodiment of a dressing assembly depicted in FIG. 1, taken along line 2-2.

Referring primarily to FIGS. 1 and 2, an illustrative, non-limiting embodiment of a treatment system 100 for treating a tissue site 102, such as an incision 104, is presented. The incision 104 is shown extending through or involving epidermis 106, dermis 108, and subcutaneous tissue 110. The treatment system 100 may also be used with other tissue sites, and may be utilized with or without reduced pressure as described herein.

The treatment system 100 may include a dressing assembly 112 having a dressing bolster 114 or manifold member. In addition, the treatment system 100 may include a sealing member 116 and a reduced-pressure subsystem 118. The treatment system 100 may also include a reduced-pressure indicator 101. While the treatment system 100 is shown in the context of a reduced-pressure dressing over an incision 104, the treatment system 100 may be used on other tissue sites, including open wounds.

The dressing bolster 114 has a first side 120 and a second, inward-facing side 122. The dressing bolster 114 may be formed from any bolster material or manifold material that provides a vacuum space, or treatment space. For example, the dressing bolster 114 may be formed from a porous and permeable foam or foam-like material, a member formed with pathways, a graft, a gauze, or any combination thereof. In some embodiments, the dressing bolster 114 may be a reticulated, open-cell polyurethane or polyether foam that may be fluid permeable. Reduced pressure applied to the dressing bolster 114 may enhance the permeability of the dressing bolster 114. One such foam material may be a VAC® GranuFoam® material available from Kinetic Concepts, Inc. (KCI) of San Antonio, Tex. The term "manifold" as used herein may refer to a substance or structure that may assist in applying reduced pressure to, delivering fluids to, or removing fluids from a tissue site. A manifold may include a plurality of flow channels or pathways. The plurality of flow channels may be interconnected to improve distribution of fluids provided to and removed from the area of tissue around the manifold. Examples of manifolds may include, without limitation, devices that have structural elements arranged to form flow channels, cellular foam, such as open-cell foam, porous tissue collections, and liquids, gels, and foams that include or cure to include flow channels.

The reticulated pores of the GranuFoam® material may be helpful in carrying out the manifold function, but as stated above, other materials may be utilized. A material with a higher or lower density than the GranuFoam® material may be desirable in some embodiments. This material may have, for example, a smaller pore size than the GranuFoam® material. Among the many possible materials, the following may be used: GranuFoam® material, FXI technical foam (www.fxi.com), gauze, a flexible channel-containing member, a graft, and other similar materials. In some embodiments, ionic silver may be added to the material, such as, for example, by a micro bonding process. Other substances, such as antimicrobial agents, may also be added to the material.

A comfort layer 124 having a first side 126 and a second, inward facing side 128 may be coupled, for example, by a heat bond 130 or other suitable technique to the second, inward-facing side 122 of the dressing bolster 114. The comfort layer 124 may enhance patient comfort when the dressing bolster 114 is adjacent to the epidermis 106 of a patient. The comfort layer 124 may be any material that helps prevent skin irritation and discomfort while allowing fluid transmission through the comfort layer 124. As non-limiting examples, a woven material, an elastic material, a polyester knit textile substrate, a non-woven material, or a fenestrated film may be utilized. As another non-limiting example, an InterDry™ textile material from Milliken Chemical, a division of Milliken & Company, Inc. of Spartanburg, S.C., may be utilized. In some embodiments, the comfort layer 124 may include antimicrobial substances, such as silver.

Figure 5:
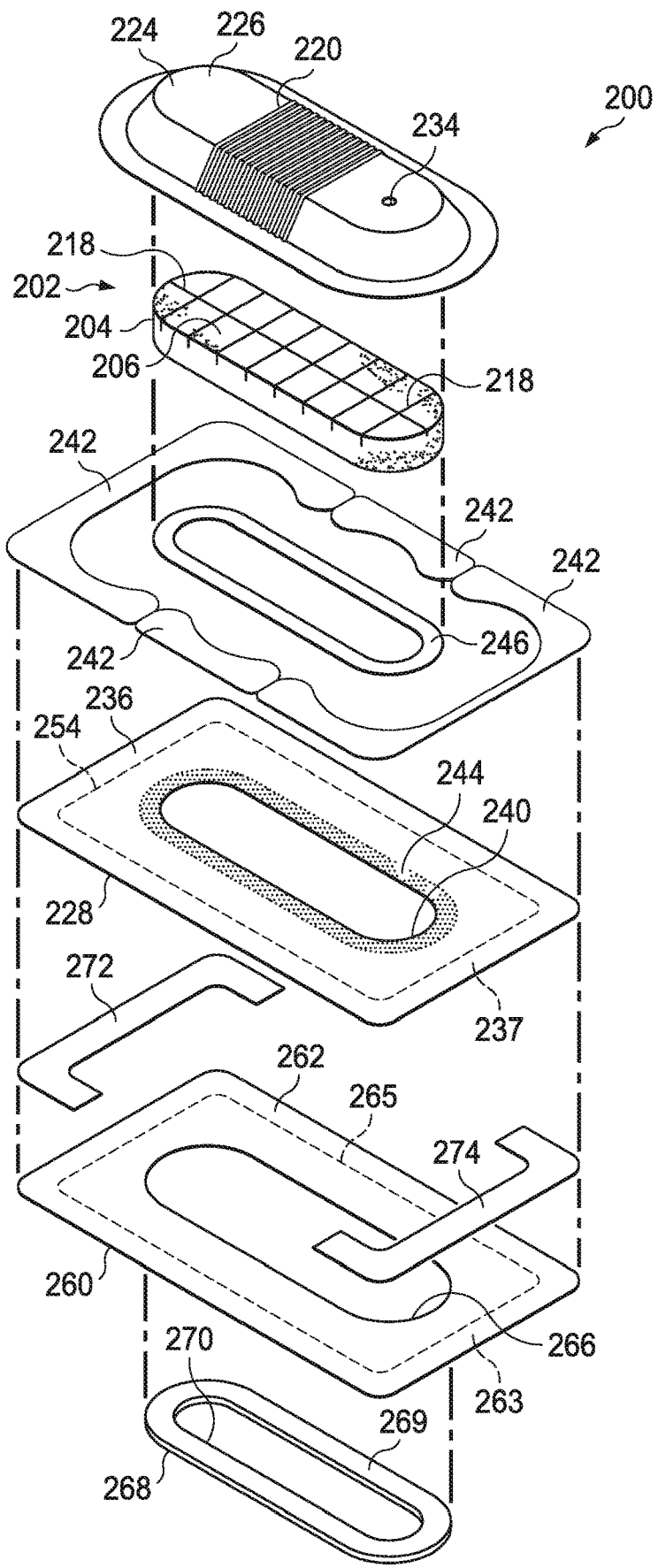
FIG. 5 is an exploded, perspective view of the dressing assembly of FIG. 4 in a state prior to assembly or deployment.

The dressing bolster 114 may include a plurality of flexibility notches or recesses, analogous to flexibility notches 218 shown in FIG. 5, for example, that may be lateral cuts in the dressing bolster 114 on the first side 120. The dressing bolster 114 may include one or more longitudinal cuts or notches. The flexibility notches may enhance the flexibility of the dressing bolster 114. The enhanced flexibility may be particularly useful when the dressing assembly 112 is applied over a joint or other area of movement on a patient. The flexibility notches may also take various shapes without limitation, such as, for example, hexagons, slits, or squares.

The dressing bolster 114 may have lateral edges (not shown) that are orthogonal with respect to the second, inward-facing side 122 of the dressing bolster 114. The lateral edges of the dressing bolster 114 may be analogous to lateral edges 205 of dressing bolster 204 depicted in FIGS. 4A and 4B. The lateral edges of the dressing bolster 114 may also have a beveled edge or angled edge. The angled or beveled edge may help distribute shear stress between the dressing bolster 114 and the epidermis 106 of a patient. The lateral edges of the dressing bolster 114 may substantially correspond to lateral edges (not shown) of the comfort layer 124.

The sealing member 116 may provide a fluid seal over the dressing bolster 114 and at least a portion of the epidermis 106 of the patient. As such, the sealing member 116 may be formed from any material that allows for a fluid seal. "Fluid seal," or "seal," may be a seal adequate to maintain reduced pressure at a desired site given the particular reduced-pressure source or subsystem involved. The sealing member 116 may be sealed against the epidermis 106, or against a gasket or drape, by a sealing apparatus, such as, for example, a pressure-sensitive adhesive.

The sealing apparatus may take numerous forms, such as an adhesive sealing tape, drape tape, or strip; double-side drape tape; pressure-sensitive adhesive; paste; hydrocolloid; hydrogel; or other suitable sealing device. If a tape is used, the tape may be formed of the same material as the sealing member 116 with a pre-applied, pressure-sensitive adhesive. The pressure-sensitive adhesive may be applied on a side of the sealing member 116 adapted to face the epidermis 106, such as an inward-facing side of the sealing member 116. The pressure-sensitive adhesive may provide a fluid seal between the sealing member 116 and the epidermis, and may be utilized in combination with a gasket or drape against the epidermis 106. Before the sealing member 116 is secured to the epidermis 106, removable strips or release liners that cover the pressure-sensitive adhesive may be removed.

The sealing member 116 may be an elastomeric material or any material or substance that provides a fluid seal. "Elastomeric" may refer to a material having the properties of an elastomer, such as a polymeric material that has rubber-like properties. Some elastomers may have ultimate elongations greater than 100% and a significant amount of resilience. The resilience of a material may refer to the ability of the material to recover from an elastic deformation. Examples of elastomers may include, without limitation, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Further, sealing member materials may include a silicone drape, a 3M Tegaderm® drape, an acrylic drape, such as one available from Avery Dennison, or an incise drape.

The sealing member 116 may be comprised of a material having a high moisture vapor transmission rate (MVTR). Use of a high MVTR material for the sealing member 116 may permit moisture vapor to pass through the sealing member 116, external to the dressing assembly 112, while maintaining the fluid seal described above.

The sealing member 116 may include a first sealing member portion 132 and a second sealing member portion 134. The first sealing member portion 132 may extend over the first side 120 of the dressing bolster 114. The sealing member 116 may extend further to form a sealing member flange, or sealing member extension 136, which has a first side (not shown) and a second, inward-facing side (not shown). The second, inward-facing side of the sealing member extension 136 may be adapted to face the epidermis 106. An aperture (not shown) may be formed on a portion of the sealing member 116 to allow fluid communication with a conduit interface 138, which may be part of a reduced-pressure assembly 140. The aperture on the sealing member 116 may be analogous to aperture 234 depicted in FIG. 3.

The second, inward-facing side of the sealing member extension 136 may be placed on a first side (not shown) of the second sealing member portion 134, and coupled thereto, such as by an adhesive, a bond 135, a weld (e.g., ultrasonic or RF welding), or by cements. The first side of the second sealing member portion 134 may face away from the epidermis 106. In another embodiment, the first sealing member portion 132 and the second sealing member portion 134 may be integrally formed with one another. The first sealing member portion 132 may include a plurality of bellows 142, folds, or stretch zones. The bellows 142 may provide additional drape material when needed to respond to stretching or other movement. For example, if the dressing assembly 112 is used on a joint, when the joint is flexed, the bellows 142 may provide additional drape material to facilitate such movement.

Prior to application, one or more release members (not shown) may be releasably coupled to the first side of the second sealing member portion 134. The release members may be analogous to release members 242 depicted in FIG. 5, and may provide stiffness to assist with, for example, deployment of the dressing assembly 112. The release members may be, for example, casting paper or a film held on the first side of the second sealing member portion 134. Each release member may have a release agent disposed on a side of the release member configured to contact a component of the dressing assembly 112, such as the second sealing member portion 134, or other components described below. In some embodiments, the release agent may be a silicone coating and may have a release factor between about 5 grams per centimeter to about 15 grams per centimeter. In other embodiments, the release factor may be between about 2 grams per centimeter to about 6 grams per centimeter. The release agent may facilitate removal of the release member by hand and without damaging or deforming the dressing assembly 112.

Release members suitable for use with the embodiments described herein may be, for example, polyester release members specified as FRA 301(T-36) and FRA 396-T13, available from Fox River Associates, LLC of Geneva, Ill. The polyester release members may be a polyethylene terephthalate (PET) release member as described below. In some embodiments, the release members may have a film thickness between about 30 microns to about 70 microns. In other embodiments, the film thickness between about 47 microns to about 53 microns. Further, the release members may have a tensile break strength in a machine direction between about 9 kilograms per square millimeter to about 15 kilograms per square millimeter. In a transverse direction, or direction transverse to the machine direction, the release members may have a tensile break strength between about 15 kilograms per square millimeter to about 23 kilograms per square millimeter. The elongation at break of the release members in both the machine direction and the transverse direction may be between about 40 percent to about 140 percent. The release members may have a shrinkage in the machine direction between about 0.0 percent to about 2.5 percent, and a shrinkage in the transverse direction between about 0.0 percent to about 1.2 percent.

The reduced-pressure subsystem 118 may include a reduced-pressure source 144. The reduced-pressure source 144 may provide reduced pressure as a part of the treatment system 100. The reduced-pressure source 144 may be fluidly coupled to the conduit interface 138 by a delivery conduit 148. The reduced-pressure source 144 may be any device for supplying a reduced pressure, such as a vacuum pump, wall suction, or other source. The reduced pressure developed by the reduced-pressure source 144 may be delivered through the delivery conduit 148 to the conduit interface 138. The conduit interface 138 may allow the reduced pressure to be delivered through the sealing member 116 to the dressing bolster 114. In some embodiments, the conduit interface 138 may provide fluid communication external to the sealing member 116 without the application of reduced pressure.

As used herein, "reduced pressure" may refer to a pressure less than the ambient pressure at a tissue site being subjected to treatment, such as the tissue site 102. The reduced pressure may be less than the atmospheric pressure. The reduced pressure may also be less than a hydrostatic pressure at a tissue site. Unless otherwise indicated, quantitative values of pressure stated herein are gauge pressures. While the amount and nature of reduced pressure applied to a tissue site may vary according to the application, the reduced pressure may be, for example, between about −5 mm Hg (−667 Pa) to about −500 mm Hg (−66.7 kPa). In some embodiments, the reduced pressure may be between about −75 mm Hg (−9.9 kPa) to about −300 mm Hg (−39.9 kPa).

The reduced pressure delivered to the dressing bolster 114 may be constant or variable, patterned or random, and may be delivered continuously or intermittently. Although the terms "vacuum" and "negative pressure" may be used to describe the pressure applied to a tissue site, the actual pressure applied to the tissue site may be more than the pressure normally associated with a complete vacuum. Consistent with the use herein, unless otherwise indicated, an increase in reduced pressure or vacuum pressure may refer to a relative reduction in absolute pressure.

The reduced-pressure source 144 is shown in FIG. 1 as having a reservoir region 146, or canister region. An interposed membrane filter (not shown), such as hydrophobic or oleophobic filter, may be interspersed between the reduced-pressure delivery conduit 148 and the reduced-pressure source 144. One or more devices, such as a representative device 150, may be fluidly coupled to the reduced-pressure delivery conduit 148. The representative device 150 may be, for example, another fluid reservoir, a collection member to hold exudates and other fluids removed, a pressure-feedback device, a volume detection system, a blood detection system, an infection detection system, a flow monitoring system, or a temperature monitoring system. Multiple representative devices 150 may be included. One or more of the representative devices 150 may be formed integrally with the reduced-pressure source 144.

In providing treatment with the treatment system 100, it may be desirable to know that reduced pressure of at least a certain threshold level is being delivered to the tissue site 102. The reduced-pressure indicator 101 may indicate such a threshold pressure. The reduced-pressure indicator 101 may be a separate unit fluidly coupled to the sealing member 116 such that reduced pressure from within the sealed space of the sealing member 116 reaches the reduced-pressure indicator 101. In some embodiments, as shown in FIG. 1, the reduced-pressure indicator 101 may be associated with the conduit interface 138 as a part of the reduced-pressure assembly 140. When adequate reduced pressure is present, the reduced-pressure indicator 101 may assume a collapsed position. When inadequate reduced pressure is present, the reduced-pressure indicator 101 may assume a non-collapsed position.

Referring primarily to FIG. 2, a sealing ring 117 may be added to the dressing assembly 112. The sealing ring 117 may enhance or otherwise provide a fluid seal around the tissue site 102, such as the incision 104. The epidermis 106 may have recesses, cracks, wrinkles, or other discontinuities on a surface of the epidermis 106 that may cause leaks. Moreover, folds, buckles, wrinkles, or other discontinuities may form in the sealing member 116 and cause leaks. These discontinuities may be a considerable issue for low flow treatment systems. The sealing ring 117 may help seal any such skin or sealing member discontinuities around the tissue site 102.

The sealing ring 117 may be adapted to be positioned between the dressing assembly 112 and the epidermis 106 and/or the tissue site 102. The sealing ring 117 may be formed, as an illustrative example, by applying or bonding a ring of sealing material to the dressing assembly 112. The sealing material may include hydrocolloids, hydrogels, silicone polymers (both crosslinked and uncrosslinked gels), and natural gums (xanthan, guar, cellulose). The sealing material may include other soft polymer gels, such as, for example, those based on polyurethanes, polyolefin gels, and acrylics.

The sealing ring 117 may be deployed by hand or extruded from an applicator, such as a syringe, to form a ring prior to application of the dressing assembly 112 to the tissue site 102. Sealing materials suitable for application by extrusion may include water soluble gums such as xanthan, guar, or cellulose, and thick greases, such as silicones. In another embodiment, the sealing ring 117 may be bonded in any suitable manner, such as, for example, by a heat bond, to the second, inward facing side 128 of the comfort layer 124 during manufacture of the dressing assembly 112. In this manner, the sealing ring 117 may be adapted to be positioned between the comfort layer 124 and the epidermis 106 and/or the tissue site 102.

In one embodiment, the sealing ring 117 may include an absorbent. For example, the sealing ring 117 may be a hydrocolloid comprising an absorbent, such as carboxy methyl cellulose (CMC). The absorbent may permit the sealing ring 117 to absorb fluid from the tissue site 102 in addition to enhancing the fluid seal around the tissue site 102. The sealing ring 117 including the absorbent may enhance the ability of the dressing assembly 112 to manage and direct fluid away from the tissue site 102 for keeping the tissue site 102 dry. For example, the dressing bolster 114 may have a thickness between the first side 120 and the second, inward-facing side 122 of the dressing bolster 114. The thickness of the dressing bolster 114 may define at least a portion of a thickness of the dressing assembly 112. The sealing ring 117 may be adapted to be positioned between the dressing assembly 112 and the tissue site 102, as described above, and around or surrounding a circumference of the tissue site 102. Relative to the dressing assembly 112, the sealing ring 117 may be positioned, for example, around, on, or at the lateral edges of the dressing bolster 114 and/or the comfort layer 124. Further, the sealing ring 117 may be positioned around or surrounding a circumference of the dressing bolster 114 and/or the comfort layer 124. Further, the sealing ring 117 may be positioned around at least a portion of the dressing bolster 114 or the comfort layer 124 that is configured to be positioned directly against or in direct contact with the tissue site 102. At least a portion of the dressing bolster 114 and/or the comfort layer 124 may be exposed and configured to be positioned directly against the tissue site 102 when the sealing ring 117 is positioned on the dressing assembly 112. Further, in such embodiments, the sealing ring 117 may surround the exposed portion of the dressing bolster 114 and/or the comfort layer 124.

The absorbent in the sealing ring 117 may wick or draw fluid in a lateral direction within the dressing assembly 112, normal to the thickness of the dressing bolster 114, and toward the lateral edges of the dressing bolster 114 for absorption in the sealing ring 117. Thus, fluid from the tissue site 102 may be wicked or otherwise drawn in a lateral direction along the surface of the tissue site 102 toward the lateral edges of the dressing bolster 114 and into the sealing ring 117. Further, fluid from the tissue site 102 may also flow through the thickness of the dressing assembly 112 and the dressing bolster 114 at least by operation of the manifold material comprising the dressing bolster 114, described above.

Figure 3:
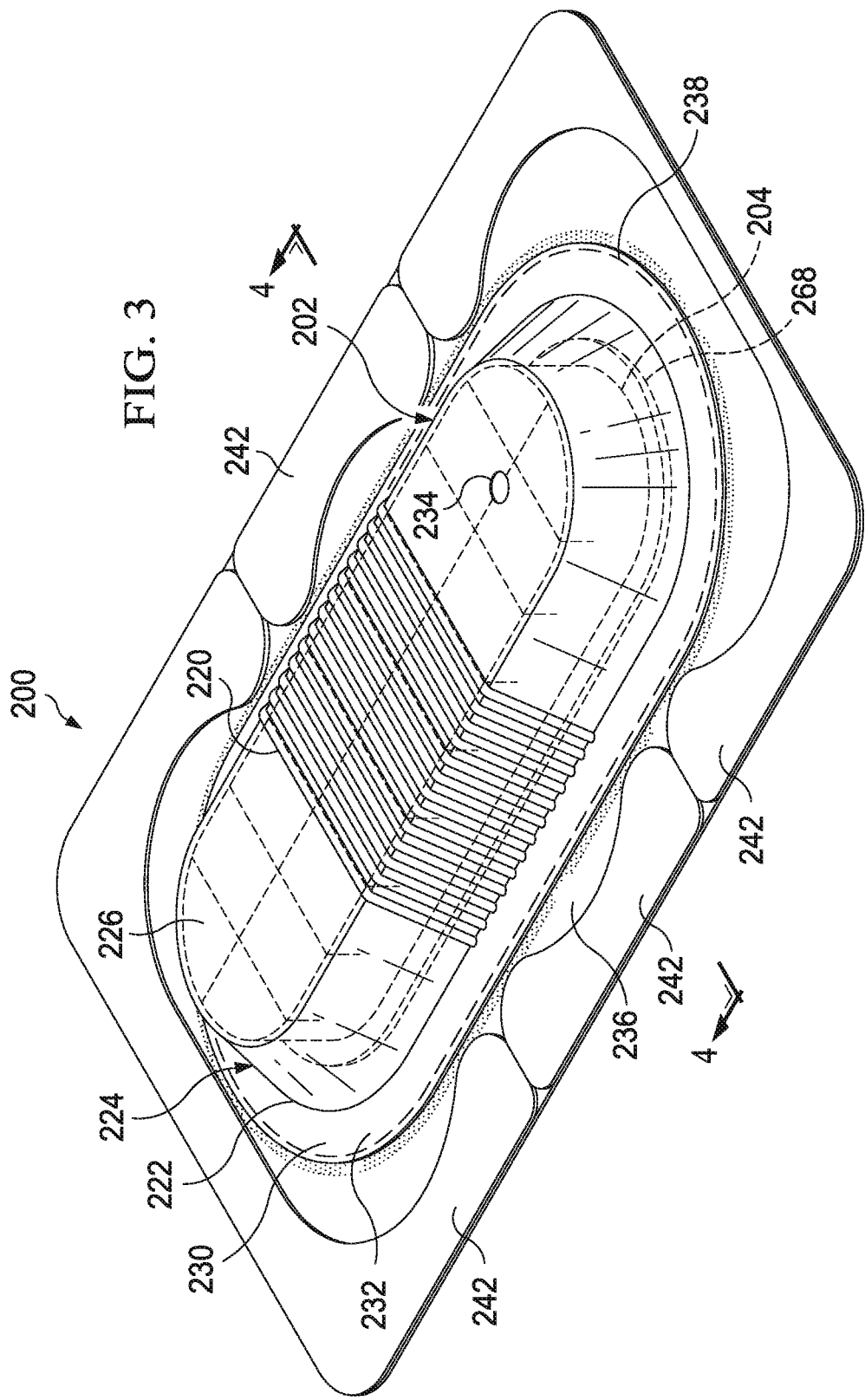
FIG. 3 is a perspective view of an illustrative embodiment of a portion of a treatment system for treating a tissue site.
Figure 4:
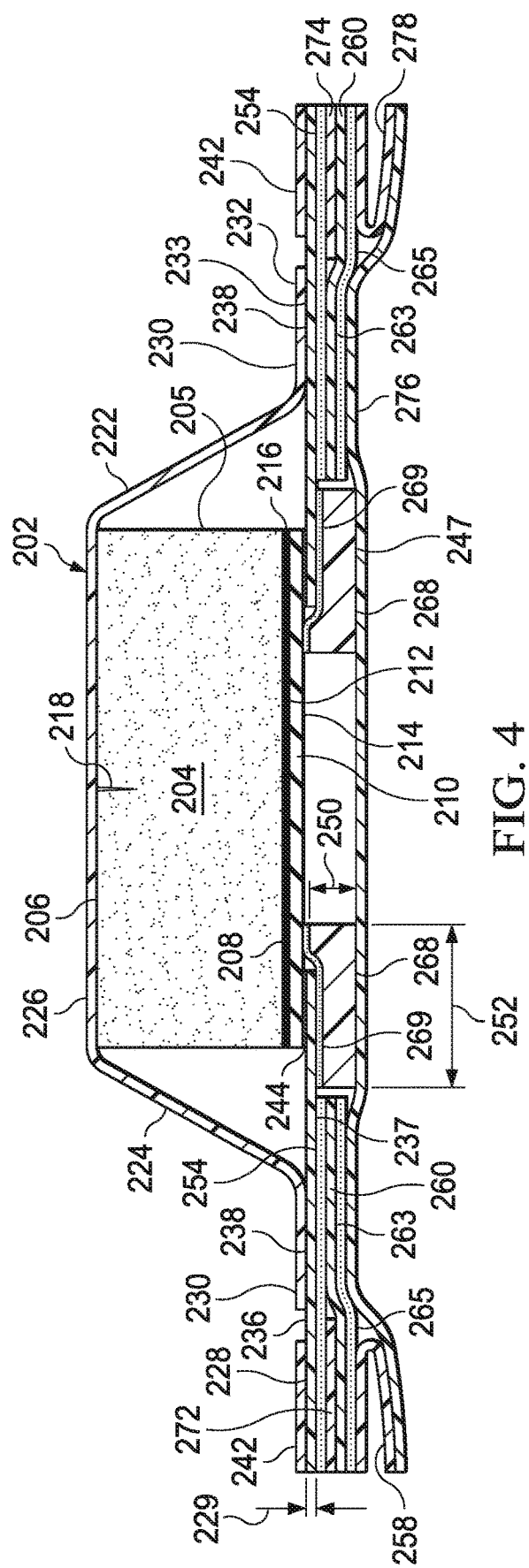
FIG. 4 is a cross-section of an illustrative embodiment of a dressing assembly depicted in FIG. 3, taken along line 4-4.

Referring now primarily to FIGS. 3-5, depicted is a portion of a treatment system 200 suitable for treating, for example, a linear wound, area wound, other wound, or a graft. FIGS. 3-5 depict the treatment system 200 in a pre-deployment state. The treatment system 200 includes a dressing assembly 202, and the dressing assembly 202 includes a dressing bolster 204. The dressing bolster 204 has a first side 206 and a second, inward-facing side 208. The dressing bolster 204 may be formed from any suitable bolster material, or manifold material, as previously referenced in connection with the dressing bolster 114. A comfort layer 210, which has a first side 212 and a second, inward-facing side 214, may be coupled, such as, for example, by a heat bond 216 or other suitable technique to the second, inward-facing side 208 of the dressing bolster 204.

The comfort layer 210 may be any material that helps prevent skin irritation and discomfort while allowing fluid transmission through the comfort layer 210. Suitable materials for the comfort layer 210 have been mentioned in connection with the comfort layer 124 of FIGS. 1-2. In some embodiments, the comfort layer 210 may include antimicrobial substances, such as silver. Further, in some embodiments, the comfort layer 210 may be made as a breathable, dry layer.

In some illustrative embodiments, the dressing bolster 204 may include a plurality of flexibility notches 218. The flexibility notches 218 may extend partially through or completely through the dressing bolster 204. The flexibility notches 218 may be lateral notches, or lateral cuts, in the dressing bolster 204. The flexibility notches 218 may also be one or more longitudinal notches, longitudinal cuts, or other cuts. The cuts may be made using a saw, a notched blade, a hot knife, or other device. The flexibility notches 218 may enhance the flexibility of the dressing bolster 204. The enhanced flexibility may be particularly useful when the dressing assembly 202 is applied over a joint or other area of movement on a patient. For example, if the dressing bolster 204 is used on a knee, the dressing bolster 204 may need to flex or extend as much as 100% or more. The flexibility notches 218 may provide such flexibility.

The dressing bolster 204 may have lateral edges 205 that are orthogonal with respect to the second, inward-facing side 208 of the dressing bolster 204. The lateral edges 205 may also have a shape, such as, for example, a beveled, angled, or rounded shape. The lateral edges 205, when angled, may be between about 10 degrees to about 90 degrees with respect to the second, inward-facing side 208 of the dressing bolster 204. The shaped lateral edges 205 may reduce shear stress between an epidermis of a patient and the dressing bolster 204. Other dimensions, steps, and processes may be used.

In some illustrative embodiments, the dressing bolster 204 may be manufactured from a foam block of Granufoam® material. The Granufoam® material may be, for example, a foam block having the dimensions of 1.21 meters×1.8 meters×0.5 meters. The foam block may be cut to have a 19 millimeter height, and a saw may be used to form lateral grooves, such as the flexibility notches 218, in the foam block. A dry layer, such as the comfort layer 210, may be laminated or otherwise attached to the second, inward-facing side 208 of the dressing bolster 204. The foam block may be cut, for example, utilizing a die cutter to form a plurality of dressing bolsters.

A sealing subsystem 222 may provide a fluid seal over the dressing assembly 202 and at least a portion of an epidermis of a patient. The sealing subsystem 222 may include a sealing member 224. The sealing member 224 may be formed with an upper drape portion or first sealing member portion 226 and a lower drape portion or second sealing member portion 228. The first sealing member portion 226 may extend over the first side 206 of the dressing bolster 204 to form a drape flange, or drape extension 230. The drape extension 230 has a first side 232 and a second, inward-facing side 233. The second, inward-facing side 233 of the drape extension 230 may be adapted to face a tissue site of a patient as described above. An aperture 234 may be formed on the first sealing member portion 226. The aperture 234 may provide fluid communication with a conduit interface (not shown). The conduit interface may be analogous to the conduit interface 138 in FIG. 1.

The second sealing member portion 228 may have a first side 236 and a second, inward-facing side 237 adapted to face a tissue site as described above. The second, inward-facing side 233 of the drape extension 230 may be placed on the first side 236 of the second sealing member portion 228, and may be coupled to the first side 236 by an attachment device 238. The attachment device 238 may be, for example, an adhesive, a bond, a weld (e.g., ultrasonic or RF weld), cements, stitching, staples, or other coupling device. The second sealing member portion 228 may include an attachment apparatus on the second, inward-facing side 237 as described below. The second sealing member portion 228 may also include a treatment area aperture 240, depicted in FIG. 5, that may be adapted to permit fluid communication through the second sealing member portion 228 and, for example, between a tissue site and the dressing bolster 204. The treatment area aperture 240 may also provide an opening for at least a portion of the dressing bolster 204, or the comfort layer 210, to be positioned directly against an epidermis and/or a tissue site of a patient. The second sealing member portion 228 also may include a dressing sealing device 254 disposed on the second, inward-facing side 237 of the second sealing member portion 228. The dressing sealing device 254 may be, for example, an adhesive adapted to cover all or a portion of the second, inward-facing side 237 of the second sealing member portion 228.

The first sealing member portion 226 may include a plurality of folds 220 or bellows to facilitate movement as described above. The folds 220 may allow the first sealing member portion 226 to expand. For example, if the dressing assembly 202 is used on a joint, when the joint is flexed, additional drape material from the folds 220 may be released to facilitate movement of the first sealing member portion 226. The folds 220 may also be formed as ridges having the cross-sectional shape of an accordion that provides additional drape material when flattened or stretched, for example.

One or more release members 242 may be releasably coupled to the first side 236 of the second sealing member portion 228, such as, for example, with an adhesive (not shown) applied on at least a portion of the first side 236. Four of the release members 242 are shown in the illustrative embodiment of FIG. 3. The release members 242 may provide stiffness to the second sealing member portion 228, and may cover the adhesive or other attachment apparatus to provide a grasping surface during deployment of the dressing assembly 202. The release members 242 may be casting paper or a film held on the first side 236 of the second sealing member portion 228.

The first side 236 of the second sealing member portion 228 may include an adhesive 244 adapted to retain the dressing bolster 204 against the second sealing member portion 228 during assembly and usage. A center release member 246 may cover and protect the adhesive 244 prior to assembly. The release members 242 that may provide stiffness to the sealing member 224 during deployment may be positioned outboard of the adhesive 244 on the first side 236 of the second sealing member portion 228.

The treatment system 200 may also include a base member 260 as a component of the dressing assembly 202 or as a component of the sealing subsystem 222. The base member 260 may be an elastomeric material or any material or substance that provides a fluid seal as described above with respect to sealing member 116. The base member 260 also may be comprised of a material having a high moisture vapor transmission rate (MVTR) as described above with respect to sealing member 116. The base member 260 may have a first side 262 and a second, inward-facing side 263 adapted to face a tissue site. The base member 260 may include a viewing aperture 266 that may be adapted in part to permit fluid communication through the base member 260 and between a tissue site and the dressing bolster 204. The base member 260 also may include a base sealing device 265 disposed on the second, inward-facing side 263 of the base member 260. The base sealing device 265 may be, for example, an adhesive adapted to cover all or a portion of the second, inward-facing side 263 of the base member 260. The base sealing device 265 may be placed against a portion of the epidermis of a patient and around a tissue site that may include a linear wound as described above.

The dressing assembly 202 also may include dressing release members 272 and 274 that may be releasably coupled to the inward-facing side 237 of the second sealing member portion 228 to cover and protect the dressing sealing device 254 prior to assembly. In one embodiment, the dressing release members 272 and 274 may sized so that they do not cover a sealing portion of the dressing sealing device 254 proximate the treatment area aperture 240 to ensure that the dressing sealing device 254 provides a complete seal with the first side 262 of the base member 260 after assembly. The dressing release members 272 and 274 may be releasably coupled within the adhesive (not shown) applied on at least a portion of the side facing the second sealing member portion 228. The dressing release members 272 and 274 may be comprised of a soft and flexible material such as a polyester film that may be polyethylene terephthalate (PET). The dressing release members 272 and 274 may be left in place during treatment and used as handles to separate the second sealing member portion 228 and remove the entire dressing assembly 202 from the base member 260 in order to inspect an incision at the tissue site through the viewing aperture 266. The dressing release members 272 and 274 may be positioned at opposite ends of the second sealing member portion 228 perpendicular to the incision rather than parallel to the incision to reduce the risk of reopening the incision as a result of pulling the second sealing member portion 228 across the length of the incision.

Even though the dressing release members 272 and 274 cover a portion of the dressing sealing device 254, the dressing sealing device 254 may be placed on the first side 262 of the base member 260 so that the second sealing member portion 228 may be removably coupled to the first side 262 of the base member 260 by the dressing sealing device 254. The dressing sealing device 254 may be adapted to couple and hold the second sealing member portion 228 against the base member 260 when being used during therapy, and further adapted to permit the removal and replacement of the second sealing member portion 228 along with the dressing assembly 202 from the base member 260. When the dressing assembly 202 is removed, the tissue site may be viewed through the viewing aperture 266 and inspected during treatment of the tissue site without removing the base member 260 and breaking the seal with the epidermis which can be painful and impede the healing process of the incision. The dressing release members 272 and 274 provide handles to the second sealing member portion 228 as a grasping surface during deployment of the dressing assembly 202 and may be adapted to remain in place to facilitate removal of the second sealing member portion 228 from the base member 260 when desirable to remove the dressing assembly 202 in order to inspect the incision at the tissue site.

The base sealing device 265 may be adapted to retain the base member 260 against the epidermis during usage and during inspection of the tissue site when the second sealing member portion 228 is removed from the base member 260 as described above. The base sealing device 265 may be, for example, an acrylic adhesive having a peel strength of approximately 4.2N/25 mm such as, for example, Tegaderm® 9833 available from 3M, and the dressing sealing device 254 may be, for example, an acrylic adhesive having a peel strength of approximately 1.4N/25 mm such as, for example, Tegaderm® 9832F also available from 3M. In another example embodiment, the base sealing device 265 may be an acrylic adhesive having a peel strength greater than about 4.0N/25 mm, and the dressing sealing device 254 may be an acrylic adhesive having a peel strength of less than about 2.0N/25 mm.

Because the peel strength of the base sealing device 265 is greater than the peel strength of the dressing sealing device 254, the second sealing member portion 228 along with the rest of the dressing assembly 202 may be separated from the base member 260 without the base member 260 being removed from the epidermis. Thus the dressing assembly 202 may be removed and changed as needed while preserving the seal between the base member 260 and the epidermis. Clinicians and caregivers are often prevented from periodically viewing and inspecting surgical incisions for up to seven days or more. Conventional procedures require that surgical incisions should be viewed and inspected at least once per day and to have dressing changes as needed. A dressing assembly that utilizes two sealing devices such as, for example, the base sealing device 265 and the dressing sealing device 254 wherein the peel strength of the former is greater than the later, allows the physician or caregiver to remove the dressing assembly 202 from the tissue site while leaving the seal with the epidermis intact. The physician or caregiver is able to remove the dressing assembly from the tissue site without disrupting the attachment and/or seal between the epidermis and the dressing assembly which facilitates daily inspection of the surgical incision through the viewing aperture 266. If necessary, any portion of the dressing may be replaced at the same time as described above.

In another example embodiment of the dressing assembly 202, the peel strength of the base sealing device 265 and the peel strength of the dressing sealing device 254 may have a peel ratio equal to the peel strength of the base sealing device 265 to the peel strength of the dressing sealing device 254. In one example embodiment, the peel ratio may be greater than about 2:1 so that the second sealing member portion 228 along with the rest of the dressing assembly 202 may be separated from the base member 260 without the base member 260 being removed from the epidermis thus preserving the seal between the base member 260 and the epidermis. In another example embodiment, the peel ratio may be greater than about 3:1 so that the second sealing member portion 228 along with the rest of the dressing assembly 202 may be separated from the base member 260 without the base member 260 being removed from the epidermis. In yet another example embodiment, the peel ratio may be in a range from about 2:1 to about 6:1. And in yet another example embodiment, the peel ratio may be in a range from about 3:1 to about 6:1.

The dressing assembly 202 may include a sealing ring 268. Analogous to the sealing ring 117, the sealing ring 268 may help seal any wrinkles or discontinuities in the epidermis or drape that might otherwise cause leaks. The sealing ring 268 may be used in addition to, or in lieu of, the sealing ring 117 that may be disposed between the inward-facing side 263 of the base member 260 and the epidermis. The sealing ring 268 may be, for example, positioned to cover a portion of the second, inward-facing side 237 of the second sealing member portion 228. The sealing ring 268 may be coupled directly to the dressing assembly 202, or coupled with an optional sealing-ring attachment device 269, such as an acrylic adhesive, cement, or other coupling device. In other embodiments, the sealing ring 268 may be coupled to the inward-facing side 208 of the dressing bolster 204, and/or to an adjacent layer, such as the comfort layer 210. The sealing ring 268 may straddle an edge of the dressing bolster 204, or otherwise extend beyond an edge of the dressing bolster 204, as depicted in FIG. 4. In other embodiments, the dressing bolster 204 may entirely overlap the sealing ring 268.

The sealing ring 268 also may include a treatment aperture 270 adapted to permit fluid communication between a tissue site and the dressing bolster 204. The perimeter of the sealing ring 268 may be bounded by the viewing aperture 266 of the base member 260 as shown in FIG. 4 and by vertical dashed lines shown in FIG. 5. In this embodiment, the sealing ring 268 may remain in place on, or removed from, the tissue site when the dressing assembly 202 is removed from the tissue site. In another example embodiment (not shown), the perimeter of the sealing ring 268 may straddle the viewing aperture 266 and cover a portion of the second, inward-facing side 263 of the base member 260. In this embodiment, the sealing ring 268 would remain in place when the dressing assembly 202 is removed from the tissue site. Although reference is made to a "ring," discrete individual members, including linear members, may comprise the sealing ring 268.

The sealing ring 268 may comprise a sealing material, such as, for example, any of the sealing materials previously described in connection with the sealing ring 117, or other material that provides initial tack between the dressing assembly 202 and an epidermis of a patient. Further, the sealing ring 268 may have a durometer, such as a material softness or hardness, between about 20 Shore 00 to about 90 Shore 00. In some embodiments, the durometer of the sealing ring 268 may be between about 70 Shore 00 to about 80 Shore 00. The sealing ring 268 may have a modulus of elasticity that falls between the modulus of elasticity of the second sealing member portion 228 and the modulus of elasticity of a tissue site and/or epidermis of a patient.

As shown in FIG. 4, the sealing ring 268 may have a thickness 250 and a width 252. The thickness 250 of the sealing ring 268 may be between about 0.3 millimeters to about 2.5 millimeters. In some embodiments, the thickness 250 may be between about 0.7 millimeters to about 1.25 millimeters. The width 252 of the sealing ring 268 may be between about 10 millimeters to about 30 millimeters. Other dimensions are possible. In some illustrative embodiments, the thickness 250 may be about 0.7 millimeters and the width 252 may be about 20 millimeters. Further, in some embodiments, the width 252 of the sealing ring 268 may extend beyond an edge of the dressing bolster 204 by about 10 millimeters and overlap the dressing bolster 204 by about 10 millimeters. In some embodiments, the second sealing member portion 228 may have a sealing member thickness 229 between about 0.178 millimeters to about 0.254 millimeters, or about 7 mils to about 10 mils. The ratio of the thickness 250 of the sealing ring 268 to the sealing member thickness 229 may be between about 2.75 to about 7.00.

The sealing ring 268 may include fenestrations or apertures. In some embodiments, the sealing ring 268 may comprise a patterned sealing material on the second, inward-facing side 214 of the comfort layer 210, or on the second, inward-facing side 208 of the dressing bolster 204. The pattern may be, for example, spaced islands, crossing lines of sealing material, or any other suitable pattern. The sealing ring 268 may function as a two-sided gasket that may provide a seal between the dressing assembly 202 and a tissue site and/or epidermis of a patient. For example, the sealing ring 268 may provide a seal between the dressing bolster 204, the comfort layer 210, or the second sealing member portion 228 and a tissue site and/or epidermis of a patient. The sealing ring 268 may absorb perspiration or other fluids from a tissue site. Further, the sealing ring 268 may help distribute shear forces created, for example, by the application of reduced pressure at the interface of the dressing bolster 204 and a tissue site and/or epidermis of a patient.

With reference to FIG. 4, when the dressing assembly 202 is in the pre-deployment state, the base sealing device 265 may be covered by a bottom release member 276 and side release members 278. The bottom release member 276 may cover and protect, for example, the base sealing device 265 and the sealing ring 268. The side release members 278 may also cover and protect the base sealing device 265. Similar to the release members 242, the side release members 278 may provide a grasping surface for a user to facilitate deployment of the dressing assembly 202 and, more specifically, the base member 260. The release members 242, the bottom release member 276, and/or the side release members 278 may be comprised of a polar semi-crystalline polymer, such as, for example, polyethylene terephthalate (PET). Use of a polar semi-crystalline polymer for the release members 242, the bottom release member 276, and/or the side release members 278 may substantially preclude wrinkling or other deformation of the dressing assembly 202. Any deformation of the release members 242, the bottom release member 276, and/or the side release members 278 may cause wrinkling or deformation of a component of the dressing assembly 202. The polar semi-crystalline polymer is highly orientated and resistant to softening, swelling, or other deformation that may occur when brought into contact with components of the dressing assembly 202, or when subjected to temperature or environmental variations, or sterilization. Thus, for example, when the polar semi-crystalline polymer is used in combination with the hydrocolloid described above for the sealing ring 268, the polar semi-crystalline polymer may not deform when in contact with the compounding ingredients of the hydrocolloid. In some embodiments, the release members 242, the bottom release member 276, and/or the side release members 278 may be configured to resist deformation when exposed to temperature variations between about 40 degrees Celsius to about 60 degrees Celsius, and gamma sterilization doses between about 25 kGy to about 45 kGy.

Continuing with FIGS. 3-5, according to an illustrative embodiment of operation, the bottom release member 276 may be removed to expose the base sealing device 265 on the second, inward-facing side 263 of the base member 260. Removal of the bottom release member 276 may also expose a second, inward-facing surface 247 of the sealing ring 268. The base sealing device 265 and/or the second, inward-facing surface 247 of the sealing ring 268 may be placed against a portion of an epidermis of a patient and around a tissue site that may include a linear wound as described above. The side release members 278 may be removed after applying the second sealing member portion 228. Similarly, the release members 242 on the first side 236 of the second sealing member portion 228 may be removed after applying the second sealing member portion 228. On the other hand, the release members 242 may be left in place to facilitate removal of the second sealing member portion 228 and the rest of the dressing assembly 202 in order to inspect the tissue site on a daily basis. A conduit interface may be coupled to the aperture 234 in the first sealing member portion 226, and reduced pressure may be delivered to the dressing assembly 202.

According to another illustrative embodiment, a method for treating a tissue site that may include disposing a dressing assembly such as, for example, the dressing assembly 202, proximate to the tissue site. The dressing assembly may include a dressing bolster, a sealing member including a dressing attachment device, a base member including a base attachment device, and a sealing ring as described above. The method may further comprise positioning the base attachment device on tissue surrounding the tissue site to releasably couple the base member to the epidermis surrounding the tissue site. The method may further comprise covering the dressing bolster and the tissue site with the sealing member to releasably couple the dressing attachment device to the base member to form a sealed space between the sealing member and the tissue site. The method may further comprise extracting fluid from the tissue site into the dressing assembly. The method may further comprise removing the sealing member from the base member without removing the base member from the tissue surrounding the tissue site where the base member has a peel strength greater than the peel strength of the sealing member such as, for example, where a ratio of the peel strength of the base member to the peel strength of the sealing member is greater than about 3:1. The method may further comprise replacing the sealing member on the base member after inspecting the tissue site through a viewing aperture so that negative pressure therapy treatment may continue without disrupting the seal between the base member and the epidermis surrounding the tissue site.

Regarding the manufacture of the systems and components described above, in applying and coupling a sealing member to a dressing bolster, a press may be utilized to remove any wrinkles in the sealing member. Further, the medical bolster material of the shaped dressing assembly may be cut using a die cutter, or by hand with a router.

In another embodiment (not explicitly shown), an attachment device, such as an adhesive, may be applied to the second, inward-facing side of a sealing ring to provide tackiness or enhanced tackiness between the sealing ring and an epidermis of a patient. The attachment device may be particularly beneficial when the sealing ring comprises a harder hydrocolloid than those previously mentioned, or when applied in cold conditions to provide time for the sealing material to warm up and become adequately tacky.

Although the subject matter of this disclosure has been provided by way of example in the context of certain illustrative, non-limiting embodiments, various changes, substitutions, permutations, and alterations can be made without departing from the scope of this disclosure as defined by the appended claims. For example, the treatment systems described herein may be used for tissue sites other than incisions such as, for example, wounds resulting from injuries or other medical conditions. Any feature described in connection to any one embodiment may also be applicable to any other embodiment. As such, the benefits and advantages described above may relate to one embodiment or may relate to several embodiments. Further, the steps of the methods described herein may be carried out in any suitable order, or simultaneously where appropriate.

I claim:

1. A system for treating a tissue site, comprising:
   a dressing assembly, comprising:
      a dressing bolster having a first side and a second side,
      a first sealing member covering the first side of the dressing bolster,
      a second sealing member having a first side and a second side including a treatment aperture extending through the second sealing member, a first portion of the first side being coupled to the first sealing member, and
      a first attachment device configured to be coupled to the second side of the second sealing member, wherein the first sealing member, the second sealing member, and the first attachment device are configured to provide a sealed space that covers the tissue site;
   a base layer, comprising:
      a third sealing member having a first side and a second side including a viewing aperture extending through the third sealing member and configurable to surround the tissue site, wherein the first attachment device is adapted to be releasably coupled to the first side of the third sealing member, and
      a second attachment device configured to be coupled to the second side of the third sealing member and adapted to be releasably coupled to tissue around the tissue site as defined by the viewing aperture;
   one or more dressing release members configured to be releasably coupled to at least a portion of the second side of the second sealing member and the first side of the third sealing member; and
   a reduced-pressure source configured to be coupled in fluid communication with the sealed space.

2. The system of claim 1, wherein the second attachment device has a peel strength and the first attachment device has a peel strength, and wherein the peel strength of the second attachment device is greater than the peel strength of the first attachment device.

3. The system of claim 1, wherein the second attachment device has a peel strength and the first attachment device has a peel strength, and wherein a ratio of the peel strength of the second attachment device to the peel strength of the first attachment device is greater than about 2.0.

4. The system of claim 1, wherein the first attachment device is a first adhesive and the second attachment device is a second adhesive.

5. The system of claim 1, wherein the dressing assembly further comprises a sealing ring disposed adjacent a treatment portion of the dressing bolster.

6. The system of claim 5, wherein the dressing bolster comprises at least two discrete members placed within abutting edges, and wherein the sealing ring comprises at least two discrete members that have coalesced to form an integral member.

7. The system of claim 5, wherein the sealing ring includes a viewing aperture configured to be positioned around a circumference of the treatment portion of the dressing bolster.

8. The system of claim 5, wherein the sealing ring is configured to be positioned at a lateral edge of the treatment portion of the dressing bolster.

9. The system of claim 1, wherein the dressing assembly further comprises a comfort layer coupled to the second side of the dressing bolster, and wherein at least a portion of the comfort layer is exposed and configured to be positioned directly against the tissue site.

10. The system of claim 9, wherein the dressing assembly further comprises a sealing ring disposed adjacent a treatment portion of the dressing bolster, the sealing ring being configured to surround the tissue site and the portion of the comfort layer that is exposed.

11. The system of claim 10, wherein the sealing ring comprises a sealing material laminated onto a drape ring and an adhesive coupling the drape ring to the comfort layer or to the dressing bolster.

12. The system of claim 10, wherein the sealing ring is coupled to at least a portion of the comfort layer.

13. The system of claim 1, wherein the first side of the second sealing member includes a second portion covering a portion of the second side of the dressing bolster to form a treatment portion on the second side of the dressing bolster exposed through the treatment aperture.

14. A dressing assembly for applying to a tissue site, comprising:
 a dressing bolster having a first side and a second side;
 a sealing member having a first side and a second side configured to cover the dressing bolster and to create a sealed space over the tissue site;
 a dressing attachment device configured to be coupled to the second side of the sealing member;
 a base member having a first side and a second side, the first side adapted to be releasably coupled to the sealing member by the dressing attachment device;
 a base attachment device configured to be coupled to the second side of the base member and adapted to be releasably coupled to tissue surrounding the tissue site; and
 one or more dressing release members configured to be releasably coupled to at least a portion of the second side of the sealing member and the first side of the base member.

15. The dressing assembly of claim 14, wherein the base member further includes a viewing aperture extending through the base member.

16. The dressing assembly of claim 14, wherein the base member further includes a viewing window extending through the base member.

17. The dressing assembly of claim 14, further comprising a sealing ring comprising an absorbent and having a first side and a second side, the first side of the sealing ring coupled to the second side of the dressing bolster and positioned around a circumference of the dressing bolster, at least a portion of the second side of the dressing bolster being exposed.

18. The dressing assembly of claim 17, wherein the sealing ring is positioned at a lateral edge of the dressing bolster.

19. The dressing assembly of claim 14, wherein the dressing assembly further comprises a comfort layer coupled to the second side of the dressing bolster, and wherein at least a portion of the comfort layer is exposed and configured to be positioned directly against the tissue site.

20. The dressing assembly of claim 14, wherein the dressing bolster has longitudinal cuts and lateral cuts disposed in the first side of the dressing bolster, the longitudinal cuts positioned normal to the lateral cuts.

21. The dressing assembly of claim 14, further comprising a bottom release member in contact with the second side of the base member by the base attachment device, the bottom release member configured to cover the base member and to be removable from the base member.

22. A method for treating a tissue site, comprising:
 disposing a dressing assembly proximate to the tissue site, the dressing assembly comprising a dressing bolster, a sealing member including a dressing attachment device, a base member including a base attachment device, one or more dressing release members configured to be releasably coupled to at least a portion of the sealing member and the base member, and a sealing ring coupled to the dressing bolster;
 positioning the base attachment device on tissue surrounding the tissue site to releasably coupled the base member to the tissue surrounding the tissue site;
 covering the dressing bolster and the tissue site with the sealing member to releasably couple the dressing attachment device to the base member to form a sealed space between the sealing member and the tissue site; and
 extracting fluid from the tissue site into the dressing assembly.

23. The method of claim 22, further comprising absorbing the fluid from the tissue site into the sealing ring.

24. The method of claim 22, further comprising removing the sealing member from the base member without removing the base member from the tissue surrounding the tissue site.

25. The method of claim 24, further comprising replacing the sealing member on the base member after inspecting the tissue site through a viewing aperture.

26. The method of claim 22, wherein extracting the fluid comprises applying reduced pressure to the sealed space.

27. The method of claim 22, further comprising communicating the fluid in a lateral direction within the dressing assembly toward the sealing ring.

28. The method of claim 22, wherein the sealing ring is positioned at a lateral edge of the dressing bolster and configured to surround the tissue site.

29. The system of claim 1, further comprising a bottom release member and one or more side release members configured to be releasably coupled to the second attachment device.

* * * * *